United States Patent [19]

Steichen et al.

[11] Patent Number: 4,790,952

[45] Date of Patent: Dec. 13, 1988

[54] ALKYL MONOPEROXYSUCCINIC ACID PRECURSORS AND METHOD OF SYNTHESIS

[75] Inventors: Dale S. Steichen, Livermore; Hao Ku, Pleasanton; Sheldon N. Lewis, Lafayette, all of Calif.

[73] Assignee: The Clorox Company, Oakland, Calif.

[21] Appl. No.: 897,152

[22] Filed: Aug. 14, 1986

[51] Int. Cl.⁴ .................... D06L 3/02; C11D 3/39; C07C 179/00; C07C 178/00

[52] U.S. Cl. .................... 252/186.39; 252/186.38; 252/186.42; 252/186.43; 252/186.41; 252/94; 252/95; 252/98; 252/100; 252/103; 8/111

[58] Field of Search .......... 252/186.38, 186.39, 252/186.41, 186.42, 186.43, 94, 95, 98, 100, 103; 8/111

[56] References Cited

U.S. PATENT DOCUMENTS

| | | | |
|---|---|---|---|
| 2,362,401 | 11/1944 | Reichert et al. | 252/97 |
| 4,013,581 | 3/1977 | Huber | 252/186 |
| 4,283,301 | 11/1981 | Diehl | 252/102 |
| 4,321,157 | 3/1982 | Harris et al. | 252/174.25 |
| 4,367,156 | 1/1983 | Diehl | 252/102 |
| 4,391,725 | 7/1983 | Bossu | 252/90 |
| 4,399,049 | 8/1983 | Gray et al. | 252/91 |
| 4,412,934 | 11/1983 | Chung et al. | 252/186.38 |
| 4,444,674 | 4/1984 | Gray | 252/95 |
| 4,473,507 | 9/1984 | Bossu | 260/502 R |
| 4,483,778 | 10/1984 | Thompson et al. | 252/94 |
| 4,585,150 | 4/1986 | Beacham et al. | 222/129 |
| 4,659,519 | 4/1987 | Ku | 252/186.26 X |
| 4,681,592 | 7/1987 | Hardy et al. | 252/186.38 X |

FOREIGN PATENT DOCUMENTS

| | | |
|---|---|---|
| 98129 | 1/1984 | European Pat. Off. |
| 0105672 | 4/1984 | European Pat. Off. |
| 0105673 | 4/1984 | European Pat. Off. |
| 166571 | 1/1986 | European Pat. Off. |
| 7109629 | 1/1972 | Netherlands |
| 561180 | 5/1944 | United Kingdom |
| 836988 | 6/1960 | United Kingdom |
| 864798 | 4/1961 | United Kingdom |
| 905877 | 9/1962 | United Kingdom |
| 931119 | 7/1963 | United Kingdom |

OTHER PUBLICATIONS

Sheldon N. Lewis, "Peracid and Peroxide Oxidations", *Oxidation*, vol. 1, 213-254, Marcel Dekker, Inc., N.Y., N.Y., (1969).

Kirk-Othmer, *Encyclopedia of Chemical Technology*, Third Edition, vol. 22, pp. 347-387.

McCutcheon's, *Detergents and Emulsifiers*, North American Edition, 1983, p. 17.

Chemical Abstract 59:8599.

Chemical Abstract 60:412.

Chemical Abstract 77:7707j.

*Primary Examiner*—John F. Terapane
*Assistant Examiner*—Virginia B. Caress
*Attorney, Agent, or Firm*—John A. Bucher

[57] ABSTRACT

A number of novel peracid precursors each have the general structure:

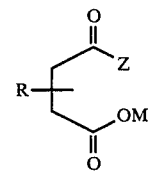

wherein: Z is a leaving group, the conjugate acid of the leaving group being in the range of from about 4 to 15; R is a substituted or unsubstituted alkyl or alkenyl group having from about 1 to 18 carbon atoms; and M is hydrogen or an alkali or alkaline earth metal. A method is also disclosed for synthesizing a product as represented above wherein succinic anhydride, including an R constituent as defined above is dissolved in a water-miscible, non-nucleophilic solvent and an acid including a Z constituent as defined above is neutralized and deprotonated to form a nucleophile, the substituted anhydride and the nucleophile being combined to form the product. The product is a component in a dry bleach product, optionally including other adjuncts.

20 Claims, No Drawings

ALKYL MONOPEROXYSUCCINIC ACID PRECURSORS AND METHOD OF SYNTHESIS

FIELD OF THE INVENTION

The present invention relates to a novel group of peracid precursors which can be combined with a source of hydrogen peroxide in aqueous solution for in situ generation of peracids capable of effective fabric bleaching. The peracid precursors and hydrogen peroxide source may, for example, be combined in a dry bleach product, with or without detergents and other suitable adjuncts.

BACKGROUND OF THE INVENTION

Hypochloride bleaches and, more recently, peroxygen bleaching compounds, such as hydrogen peroxide, sodium percarbonate and sodium perborate monohydrate or tetrahydrate, for example, have been found useful in the bleaching of fabrics, textiles, and other similar materials.

Preformed peracid chemistry has developed more recently and been found to provide bleaching action.

Now, peracid precursor or activated bleach chemistry presents further alternative bleaching compositions. Generally, this chemistry concerns the use of precursors or activators which combine in aqueous solution with a peroxygen bleaching compound to cause effective bleaching action.

There have accordingly been a number of such peracid precursors or bleach activators developed in the prior art.

For example, U.S. Pat. No. 4,283,301 issued Aug. 11, 1981 to Diehl disclosed peracid precursors in the form of esters having different leaving groups specifically identified as either enols, imidazoles or carbon acids. In this regard, the Diehl patent is similar to many other references in using the term "leaving group" to identify a substituent of a precursor molecule which rapidly cleaves off in aqueous solution and promotes formation of the desired peracid. Diehl employed the symbol Z to designate such a leaving agent within a peracid precursor and that practice is also employed in the following disclosure of the present invention.

U.S. Pat. No. 4,412,934 issued Nov. 1, 1983 to Chung et al also disclosed surface active peracid precursors, which were denoted as "bleach activators", having the general configuration or structure RCOL wherein R was an alkyl group with 5 to 18 carbon atoms and L was a leaving group, the conjugate acid of which had a pKa in the range of 6–13. GB No. 864,798, however, appears to have disclosed the same technology at an earlier time.

U.S. Pat. No. 4,483,778 issued Nov. 20, 1984 to Thompson et al disclosed a modification of a peracid precursor to the Chung et al type, particularly for the purpose of reducing or eliminating undesirable odors.

European Patent Publication Nos. 105,672 and 105,673, both published Apr. 18, 1984 upon application by the Proctor & Gamble Company, disclosed methods of synthesizing peracid precursors of the type disclosed by Chung et al.

U.S. Pat. No. 4,473,507 issued Sept. 25, 1984 to Bossu disclosed preformed peroxy acid bleach preferably employed in conjunction with a dry, granular, controlled release laundry bleach product in a water-permeable pouch.

All of the above noted peracid precursors or bleach activators and the peracids resulting in aqueous solution have been found to be effective to one degree or another in terms of bleaching activity.

There has been found to remain a need for peracid precursors having further improved characteristics. For example, in addition to providing increased bleaching action, it is also desirable to provide a peracid precursor capable of providing greater peracid yield in aqueous solution. At the same time, there has also been found to remain a need for new peracid precursors and corresponding methods for effectively synthesizing the precursors.

SUMMARY OF THE INVENTION

It is therefore an object of the invention to provide novel peracid precursors, a novel method for synthesizing the precursors and a novel bleach composition containing the precursors.

It is a further object of the invention to provide novel peracid precursors having the general structure:

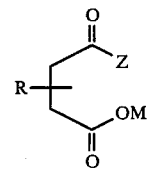

wherein
Z is a leaving group characterized by a conjugate acid thereof having a pKa value in the range of from about 4 to 15;
R is a substituted or unsubstituted, alkyl or alkenyl group having from about 1 to 18 carbon atoms, the form of the structure indicating that R can be in either the or position; and
M is hydrogen or an alkali or alkaline earth metal.

It is a further object of the invention to provide a peracid precursor compound of the general structure set forth above wherein Z is selected from the group consisting essentially of:
(1) a compound having the general structure

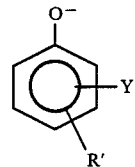

wherein
Y and R' are optionally substituted at any respective available locations in the structure,
R' is hydrogen or a substituted or unsubstituted alkyl group of about one to about ten carbon atoms, with or without an ether linkage, that is, R' or OR' where R' is otherwise defined as above, and
Y is hydrogen or a halogen or a solubilizing group; and
(2) a compound having the general structure comprising

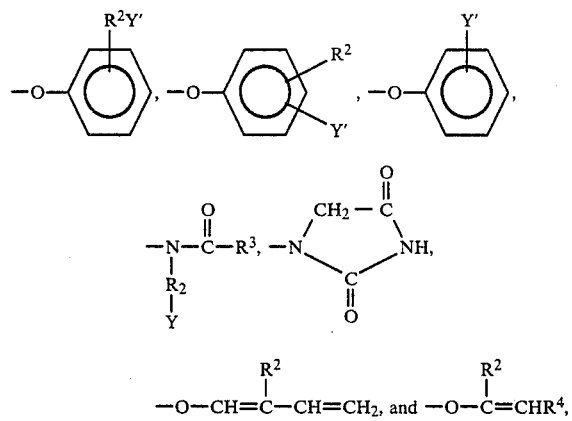

wherein
R² is an alkyl chain containing from about one to about eight carbon atoms,
wherein
R³ is an alkyl group containing from about one to about eighteen carbon atoms,
R⁴ is H or R², and
Y' is H or a solubilizing group; and
(3) the group consisting of enols, carbon acids and N-alkyl quaternary imidazoles.

It is a still further object of the invention to provide a novel peracid precursor compound wherein the leaving group Z is identified in subparagraph (2) above and wherein Y' is selected from the group consisting of $SO_3^-M$, $CO_2^-M$, $SO_4^-M$, $N^+R_3^5X$, $ONR_2^5$ and mixtures thereof wherein R⁵ is an alkyl chain containing at least one carbon atom, M is a cation and X is an anion.

In accordance with the preceding object of the invention, the specific compound noted above includes the novel base structure of the invention while further including a suitable leaving group.

It is another further object to provide a peracid precursor compound of the type noted above wherein Y is a solubilizing group selected from the group consisting of $CO_2^-M'$, $SO_3^-M'$, $N^+(^R)_3$ and OH, M' being hydrogen or an alkali or alkaline earth metal or mixtures thereof.

Preferably, the peracid precursor compound includes a phenol group or a phenol carboxylate as a leaving group with R being an alkyl group having from about 8 to 12 carbon atoms or an alkenyl group having from about 10 to 14 carbon atoms.

Peracid precursor compounds of the above type, particularly the preferred compounds noted immediately above, have been found to exhibit excellent peracid yields over a wide pH range while also lending themselves to use in bleaching compositions.

Accordingly, it is another related object to provide a dry bleaching composition and method of bleaching wherein a composition is prepared including a source of hydrogen peroxide in aqueous solution and a bleach-effective amount of a peracid precursor compound as noted above.

It is yet another further related object to provide a method for synthesizing peracid precursor compounds of the type noted above in a process wherein: succinic anhydride substituted with an R substituent as defined above is dissolved in a water miscible non-nucleophilic solvent; an acid including a Z constituent as defined above is neutralized in order to deprotonate the acid and convert it into a nucleophile also including Z as a substituent; and the substituted anhydride and nucleophile are combined in an addition reaction to form the peracid precursor compound.

It is also a general object of the invention to provide a peracid precursor compound or compounds capable of effective bleaching in bleach or wash temperatures below about 70° C., more preferably below about 60° C., and most preferably at or below about 50° C.

Additional objects and advantages of the invention are made more apparent in the following description and examples of the invention which, however, are not to be taken as limiting the scope of the invention but rather to facilitate an understanding thereof.

DESCRIPTION OF THE PREFERRED EMBODIMENTS

General Structure of the Peracid Precursor Compounds of the Invention

As noted above, the present invention generally relates to novel peracid precursor compounds which are effective to provide relatively high bleaching activity in aqueous solution or wash water at temperatures generally below about 70° C., more preferably below about 60° C. and most preferably at or below about 50° C.

The novel peracid precursors of the invention are formed with a succinic anhydride moiety which is combined, in a method of synthesis described in greater detail below, with one of a variety of leaving agents and an alkyl or alkenyl constituent selected for promoting surface activity of the resulting peracid precursor. Accordingly, the invention is based upon peracid or perhydrolysis chemistry as referred to above and dealt with at length in the prior art, for example by Sheldon N. Lewis, in Chapter 5 entitled "Peracid and Peroxide Oxidations" of the publication entitled *Oxidation*, Volume 1, published by marcel Dekker, Inc., New York, N.Y., 1969 (see pages 213-254). In order to avoid a detailed discussion of basic peracid and perhydrolysis chemistry, even though not believed necessary for an understanding of the invention by those skilled in the art, that reference is incorporated herein as though set out in its entirety.

In accordance with the above description, the preferred peracid precursor compounds of the present invention have the general structure:

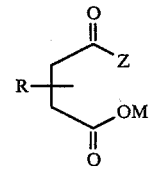

wherein
Z is a leaving group, the conjugate acid of which has a pka in the range of from about 4 to about 15;
R is a substituted or unsubstituted, alkyl or alkenyl group having from about one to about eighteen carbon atoms the form of the structure indicating that R can be in either the alpha or beta position; and
M is hydrogen or an alkali or alkaline earth metal.

A number of peracid precursor compounds corresponding to the above structure of the invention have been found to result in excellent perhydrolysis in aqueous solution, giving particularly high yields of the corresponding or desired peracid. In addition to the excellent yields noted above and discussed in greater detail below, the peracid precursor compounds of the invention have also been found to surprisingly demonstrate pH insensitivity.

In other words, the peracid precursor compounds of the invention defined by the general structure set forth above have been found to achieve increased perhydrolysis yield as compared with peracid precursors available from the prior art. Those high yields can be achieved at pH values in the range of about 8 to 10. It is also to be understood, of course, that very high perhydrolysis yields are accomplished by the peracid precursor compounds of the present invention at higher pH values.

In considering the structure of the peracid precursor compounds of the present invention in greater detail, it was noted above that the general structure includes an alkyl or alkenyl group, either substituted or unsubstituted. This substituent of the basic succinic anhydride structure promotes "surface bleaching" after undergoing perhydrolysis in wash water. The alkyl or alkenyl group, referred to above as R, produces an affinity in the peracid precursor compound for fabrics of the type being subjected to bleach treatment. Bleaching action thus occurs more effectively upon or near the surface of the fabric.

As noted above and discussed in greater detail below, R is selected as an alkyl or alkenyl group having from about 1 to about 18 carbon atoms and more preferably from about 6 to 16 carbon atoms. Most preferably, R comprises an alkyl group having from about 8 to 12 carbon atoms or an alkenyl group having from about 10 to 14 carbon atoms. As will also be noted in greater detail below, these most preferred alkyl and alkenyl groups form a substituent of the peracid precursor compound. At the same time, the leaving group, identified above as Z, preferably comprises either a phenol group or a substituted phenol group such as a phenol carboxylate or sulfonate.

Various solubilizing groups such as the sulfonates ($-SO_3^-$) or carboxylates ($-CO_2^-$) have been found to impart good solubility or dispersion characteristics to the peracid precursors of the present invention. Additionally, a counterpart ion or counterion for the solubilizing group is preferably chosen from the group consisting of hydrogen, alkali metal ions including sodium, potassium and lithium, alkaline earth metal ions and ammonium ions.

Addition of the solubilizing group can be accomplished in a number of ways well known to those skilled in the art. For example, halogen groups may be added by typical halogenation reactions in which a typical source of halogen is combined by addition with a selected starting material in the presence of a Lewis acid. Nitration, on the other hand, occurs when the starting material is reacted with nitric acid in the presence of sulfuric acid. Sulfonation occurs when the starting material is reacted with concentrated sulfuric acid. Amination is generally produced by reacting an amino source with the starting material in the presence of liquid ammonia. Further, acylation and alkylation can readily be carried out by Friedel-Crafts reactions.

As noted above, the general structure of the peracid precursor compounds includes a substituent identified as M and located on the free succinate carboxylate of the succinic anhydride structure. Although M is usually hydrogen, at least initially, it may also be an alkali or alkaline earth metal as noted above. If any of the peracid precursor compounds having the above general structure, with M being hydrogen, are placed in aqueous solution or in wash water, their very high deprotonation values in water (for example, a pKa of about 4) readily cause formation of compounds where M is any of a variety of alkali or alkaline earth metals present in the aqueous solution or wash water. Thus, these variations are considered to be equivalent to the basic hydrogenated structure.

The greatest variation for the peracid precursor compounds of the invention exists within the leaving group identified as Z. As initially noted above, the leaving group Z may be selected from a group of compounds consisting of the following:

(1) Initially, the leaving group Z may be a compound having the general structure:

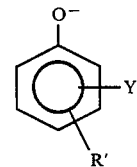

wherein

Y and R' are optionally substituted at any respective locations in the structure, R' is hydrogen or a substituted or unsubstituted alkyl group of about one to about ten carbon atoms, with or without an ether linkage, that is, R' or OR' where R' is otherwise defined as above, and Y is hydrogen or a halogen or a solubilizing group.

In the above class of leaving group compounds, R' and Y may both be hydrogen with the leaving group structure being a phenol group. Y may also be a halogen or solubilizing group, as described in greater detail below, with R' being a substituted or unsubstituted alkyl group of about 1 to 10 carbon atoms, with or without an ether linkage, that is, R' or OR' where R' is otherwise defined as above. Accordingly, a substantial number of compounds are covered by paragraph (1) above.

Also in connection with the structure of paragraph (1), the Y and R' substituents may be located at any of the unsubstituted positions in the phenol ring. Accordingly, the substituents Y and R' are shown above as being capable of addition at any available location.

It is also to be understood that numerous other substituents disclosed in the general structure of the peracid precursor compounds may similarly be located in a variety of positions. Accordingly, the preceding comments concerning the Y and R' substituents of paragraph (1) also apply to those other substituents.

(2) Yet another group of compounds suitable for forming the Z substituent in the general structure of the peracid precursor compound of the present invention may have any of the following general structures:

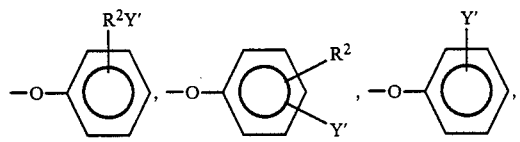

-continued

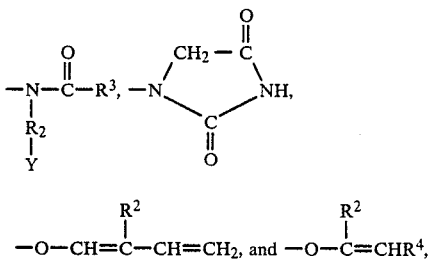

$$-O-CH=\overset{R^2}{\underset{|}{C}}-CH=CH_2, \text{ and } -O-\overset{R^2}{\underset{|}{C}}=CHR^4,$$

wherein
$R^2$ is an alkyl chain containing from about one to eight carbon atoms,
wherein
$R^3$ is an alkyl group containing from about one to eighteen carbon atoms,
wherein
$R^4$ is H or $R^2$, and
wherein
Y' is H or a solubilizing group.

The class of leaving group compounds set forth in subparagraph (2) is also a substituent of the general structure of the novel peracid precursor compounds identified above.

(3) Finally, yet another class of leaving groups Z is defined as consisting of enols, carbon acids and N-alkyl quarternary imidazoles.

Peracid precursor compounds constructed according to the present invention and including a leaving group Z as defined in subparagraph (3) have been found to exhibit the general advantages of the present invention. However, certain peracid precursor compounds with leaving groups defined in subparagraph (3), particularly those including carbon acids, may be less satisfactory for example by exhibiting lower perhydrolysis yields in aqueous solution.

As noted above, a wide variety of substituents are possible in the general structure of the peracid precursor compounds. However, the most preferred forms of the peracid precursor compounds include R as an alkyl group containing from about 8 to 12 carbon atoms or an alkenyl group containing from about 10 to 14 carbon atoms while the leaving group Z preferably comprises either a simple phenol or a substituted phenol, preferably a sulfonated phenol or a carboxylated phenol as also discussed in greater detail below.

In addition to exhibiting excellent perhydrolysis yields with corresponding pH insensitivity, the peracid precursor compounds of the general structure defined above, particularly those summarized immediately above, have also been found to particularly lend themselves to effective synthesis as disclosed in the following examples.

Surfactants and Other Detergent Adjuncts

Surfactants appear useful in the inventive compositions to improve cleaning performance. Nonionic surfactants appear particularly effective for this purpose. Preferred surfactants include linear ethoxylated alcohols, such as those sold by Shell Chemical Company under the brand name NEODOL. Other suitable nonionic surfactants include other linear ethoxylated alcohols with an average length of from about 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0–10 moles of ethylene oxide and about 1 to 10 moles of propylene oxide per mole of alcohol; linear and branched alkylphenoxy (polyethoxy) alcohols, otherwise known as ethoxylated alkylphenols with an average chain length of 8 to 16 carbon atoms and averagins 1.5 to 30 moles of ethylene oxide per mole of alcohol; and mixtures thereof.

Further suitable nonionic surfactants include polyoxyethylene carboxylic acid esters, fatty acid glycerol esters, fatty acid and ethoxylated fatty acid alkanolamides, certain block copolymers of propylene oxide and ethylene oxide, and block polymers of propylene oxide and ethylene oxide with propoxylated theylene diamine. Also included are such semi-polar nonionic surfactants as amine oxides, phosphine oxides, sulfoxides, and their ethoxylated derivatives.

Anionic surfactants may also be employed. Examples of such anionic surfactant include the alkali metal and alkaline earth metal salts of $C_6$–$C_{20}$ fatty acids and resin acids, linear and branched alkyl benzene sulfonates, alkyl sulfates, alkyl ether sulfates, alkane sulfonates, olefin sulfonates, hydroxyalkane sulfonates, fatty acid monoglyceride sulfates, alkyl glyceryl ether sulfates, acyl sarconsinates and acyl N-methyltaurides.

Suitable cationic surfactants include the quarternary ammonium compounds in which typically one of the groups linked to the nitrogen atom is a $C_{12}$–$C_{18}$ alkyl group and the other three groups are short chained alkyl groups which may have inert substituents such as phenol groups.

Further, suitable amphoteric and zwitterionic surfactants, which may contain an anionic water-solubilizing group, a cationic group and a hydrophobic organic group, include amino carboxylic acids and their salts, amino dicarboxylic acids and their salts, alkylbetaines, alkyl aminopropylbetaines, sulfobetaines, alkyl imidazolinium derivatives, certain quarternary ammonium compounds, certain quaternary phosphonium compounds and certain tertiary sulfonium compounds. Other examples of potentially suitable zwitterionic surfactants can be found in Jones, U.S. Pat. No. 4,005,029, at columns 11–15, which is incorporated herein by reference.

Further examples of anionic, nonionic, cationic and amphoteric surfactants which may be suitable for use in this invention are set forth in Kirk-Othmer, *Encyclopedia of Chemical Technology*, Third Edition, Volume 22, pages 347–387, and *McCutcheon's Detergents and Emulsifiers*, North American Edition, 1983, which are also incorporated herein by reference.

As mentioned above, the surfactants may actually assist during perhydrolysis to bring the precursor into more intimate contact with the source of hydrogen peroxide. If so, then certain water soluble or dispersible polymers such as polyvinyl alcohol, polyvinyl pyrrolidine, polyacrylic acid and the like, may also aid in promoting perhydrolysis.

As mentioned hereinabove, other common detergent adjuncts may be added if a bleach or detergent bleach product is desired. In a dry bleach composition, for example, the following ranges (set forth by weight percentages) appear suitable;

| | |
|---|---|
| Hydrogen Peroxide Source | 0.5–50.0% |
| Peracid Precursor | 0.05–75.0% |

| | |
|---|---|
| Surfactant | 1.0–50.0% |
| Buffer | 1.0–50.0% |
| Filler, stabilizers, dyes, Fragrances, brighteners, etc. | 0.5–99.9% |

The hydrogen peroxide source may be selected from the alkali metal salts of percarbonate, perboarte, hydrogen peroxide adducts and hydrogen peroxide. Most preferred are sodium percarbonate, sodium perborate mono- and tetrahydrate, and hydrogen peroxide. In liquid applications, it may be necessary to isolate the liquid hydrogen peroxide solution from the precursor prior to use, e.g., to prevent premature decomposition. This can be accomplished by dispensing separate streams of fluid containing, respectively, hydrogen peroxide and precursor and other adjuncts via, e.g., a multiple liquid dispenser. An example of a dispenser of this type is "Multiple Liquid Proportional Dispensing Device," disclosed in U.S. Pat. No. 4,585,150, issued Apr. 29, 1986 to Beacham et al, and assigned to The Clorox Company.

The buffer may be selected from sodium carbonate, sodium bicarbonate, sodium borate, boric acid, sodium silicate, phosphoric acid salts, and other alkali metal-/alkaline earth metal salts known to those skilled in the art. Organic buffers, such as succinates, maleates and acetates may also be suitable for use. It appears preferable to have sufficient buffer to attain an alkaline pH.

The filler material which, in a detergent bleach application, may actually constitute the major constituent of the detergent bleach, is usually sodium sulfate. Sodium chloride is another potential fillter. Dyes include anthraquinone and similar blue dyes. Pigments, such as ultramarine blue (UMB), may also be used, and can have a bluing effect by depositing on fabrics washed with a detergent bleach containing the UMB. Monastral colorants may also be included. Brighteners, such as stilbene, styrene and styrylnapthalene brighteners (fluorescent whitening agents), may also be used. Fragrances used for esthetic purposes are commercially available from Norda, International Flavors and Fragrances, Firmenich and Givaudon.

Synthesis of the Peracid Precursors

The novel peracid precursor compounds of the invention are synthesized by the methods summarized below and embodied by the following examples. Additionally, bleaching performance resulting from use of products of those methods are set forth below.

The method for synthesizing peracid precursors of the invention is summarized immediately below and is believed generally applicable for use with a wide variety of peracid precursor products having the general structure:

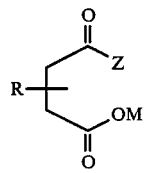

wherein Z, R and M are defined as before. Following the summary of the method of synthesization, a number of examples are then set forth for a preferred peracid precursor products according to the invention.

In discussing the synthesis method of the invention, the procedural steps are divided into seven portions referred to below as Step I through Step VII. The numbering of steps in this manner is merely intended to facilitate a better understanding of the invention and is not intended to indicate relative importance for any of the steps. In fact, as will be noted below, certain of the procedural portions or steps are considered critical to the invention while other of the steps are set froth only for the purpose of demonstrating complete synthesis and separation of the precursor products as contemplated by the invention.

In an initial processing portion referred to as Step I, an acid selected to include Z as a substituent, where Z is defined as above, is neutralized with a selected base catalyst in order to deprotonate the acid and convert it into a nucleophile suitable for entering into an addition reaction disclosed below as Step III.

By way of example, one preferred structure for Z according to the present invention is a phenol carboxylate group. In order to better demonstrate Step I of the invention for that exemplary product, p-hydroxybenzoic acid is selected as the corresponding acid. At the same time, sodium hydroxide is selected for achieving base catalysis in Step I.

Accordingly, for these exemplary materials, Step I is preferably represented as:

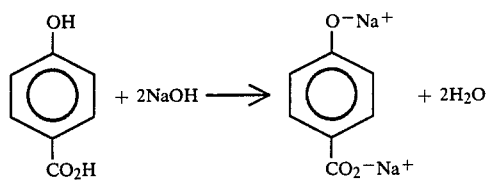

In Step I, the base catalysis agent is present in a molar excess relative to the acid, for example, in a molar ratio of 2:1, in order to assure complete conversion of the acid to the nucleophile. At the same time, the nucleophile is conditioned for entering into the addition reaction of Step III (set forth below).

In Step II, which is carried out separately from the procedure of Step I, succinic anhydride substituted with an R substituent as defined above is dissolved in a water-miscible non-nucleophilic solvent in order to assure availability of the substituted succinic anhydride in the addition reaction of Step III as described below.

In this step, it is particularly important that the solvent be non-nucleophilic so that is does not participate in the addition reaction of Step III. At the same time, the solvent must be water-miscible in order to disperse the substituted succinic anhydride, which is hydrophobic in nature, in the water phase of Step III.

As noted above, R is either an alkyl or alkenyl group having from about 1 to 18 carbon atoms, more preferably from about 6 to 16 carbon atoms and most preferably an alkyl group having from about 8 to 12 carbon atoms or an alkenyl group having from about 10 to 14 carbon atoms.

Exemplary non-nucleophilic and water-miscible solvents suitable for use in the dissolution procedure of Step II include but are not limited to tetrahydrofuran (THF), dimethyl sulfoxide (DMSO), ethyl acetate, ketones having from about 1 to 4 or 5 carbon atoms such as methyl ethyl ketone (MEK) and ethers such as dimethyl, diethyl and dipropyl ethers.

The identify of the particular solvent employed in Step II has been found to be of substantial importance within the present invention to assume completion of the substitution reaction in Step III. The above noted solvents have been found generally satisfactory for this purpose. However, tetrahydrofuran has been found to be a most particularly preferred solvent in Step II in order to assure the high yield desired in the present invention as noted above. Of the other solvents, diethyl ether was found to be suitable for use where Z included an unsubstituted phenol group but not where Z was a substituted phenol such as phenol carboxylate.

In Step III, the substituted anhydride dissolved in the water-miscible and non-nucleophilic solvent of Step II, is combined in approximately equal molar amounts with the nucleophile resulting from neutralization of the acid including Z as a constituent, in an addition reaction to form the peracid precursor product of the present invention.

Where the exemplary components discussed above in connection with Step I are employed in the method of the invention, the addition reaction of Step III may be set forth as follows:

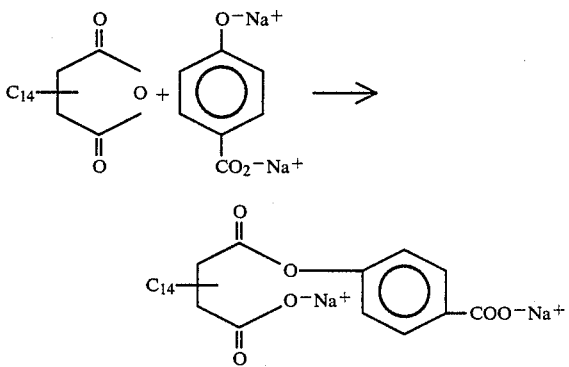

In carrying out Step III, the addition time is generally extended to as long as five minutes in the examples set forth below in order to prevent instability from occurring in the products of the addition reaction.

Because of the selection and conditioning of components as described above in Steps I and II, the addition reaction of Step III is made possible in accordance with the present invention.

Step IV of the synthesis method involves agitation or stirring of the components from Steps I and II for an additional period of time after their combination in order to assure completion of the addition reaction of Step III.

In Step V of the synthesis method, a non-nucleophilic organic solvent is added to the combination resulting from Steps III and IV to initiate extraction of an organic phase including the peracid precursor product of the invention. In order to more effectively perform the extraction step noted above, the organic non-nucleophilic solvent is preferably very polar and may be selected from the group including but not limited to non-water soluble ethers, methylene chloride, chloroform, etc.

In Step VI of the synthesis method, an acid is added to the addition reaction product together with the organic solvent from Step V in order to neutralize the excess base catalysis agent and precursor salt from Steps I and III and thereby protonate the peracid precursor product of the invention so that it enters substantially completely into the organic phase formed by the extraction solvent added in Step V.

Hydrochloric acid is a suitable acid for carrying out the function of Step VI. Other inorganic acids which appear suitable for use in the process include sulfuric acid, phosphoric acid and nitric acid.

Steps V and VI are not particularly critical to the invention in terms of forming the peracid precursor product which, as was noted above, is formed by the combined limitations of Steps I-III. However, Steps V and VI are important to the extent that they cause substantially all of the peracid precursor product to enter the organic phase formed by the extraction solvent in order to further facilitate high yield recovery which is an important feature of the invention.

Thereafter, in Step VII, the peracid precursor product contained in the organic phase is dried, for example over magnesium sulfate, and the solvent from Step V removed for example by evaporation in order to result in recovery of the product itself.

As noted above, the procedures provided in Steps I-III are particularly critical to the invention and result in formation of the desired peracid precursor product. At the same time, it is particularly important to note in connection with Steps I-III that the synthesis of the present invention can be carried out in a single container.

In the following examples, specific synthesis techniques are set forth for a number of preferred peracid precursor products according to the present invention.

EXAMPLE 1

α and β-Octyl (Mono p-Carboxy Phenol) Succinate

In this example, 22.1 grams (0.16 moles) of p-hydroxybenzoic acid, obtained from Aldrich Chemical Co., Milwaukee, Wis., was dissolved in 130 milliliters of 10% sodium hydroxide contained in a flask immersed in a cold ice bath. In a separate container, 33.9 grams (0.16 moles) of octylsuccinic anhydride were combined with 150 milliliters of tetrahydrofuran (THF), also obtained from Aldrich Chemical Co.

The substituted succinic anhydride dissolved in THF was then added over a period of about five minutes to the p-hydroxybenzoic acid neutralized in a molar excess of sodium hydroxide.

Thereafter, the reaction mixture resulting from combination of the substituted succinic anhydride and the acid was stirred for an additional period of about twenty minutes in order to assure completion of the addition reaction between the substituted succinic anhydride and the acid.

200 milliliters of ether, also obtained from Aldrich Chemical Co., were then added to the reaction mixture followed by the addition of 100 milliliters of a 20% solution of hydrochloric acid. This results in phase separation with the peracid precursor product of the invention entering into the organic phase formed primarily by the ether solvent. The organic phase including the ether solvent and peracid precursor product was then separated from the water phase and dried over magnesium sulfate in order to remove any residual water. Thereafter, the organic phase was subjected to a reduced pressure of about 20 millimeters of mercury (mm. Hg) in order to effect removal of the ether solvent from the product. This resulted in the formation of 52.4 grams of the subject peracid precursor product as a white solid substance. The resulting product included alkyl groups in a mixture of α and β positions as indicated by the title of EXAMPLE 1 and corresponding to the initial octylsuccinic anhydride.

EXAMPLE 2

α and β-Decyl (Mono p-Carboxy Phenol) Succinate

The steps of Example 1 were again followed except that 38.4 grams (0.16 moles) of decylsuccinic anhydride, also obtained from Humphrey Chemical Co., were dissolved in THF in place of the octylsuccinic anhydride of Example 1. Otherwise, the steps of Example 1 were repeated as set forth above resulting in the formation of 56.3 grams of the subject peracid precursor product also in the form of a white substance.

EXAMPLE 3

α and β-Dodecyl (Mono p-Carboxy Phenol) Succinate

The steps of Example 1 were again repeated except that 42.9 grams (0.16 moles) of dodecylsuccinic anhydride were dissolved in the THF. At the same time, the acid was dissolved in 130 milliliters of a 10% solution of sodium hydroxide in order to provide a greater liquid or water volume as discussed above. The dodecylsuccinic acid was also obtained from Humphrey Chemical Co. The steps of Example 3 resulted in the formation of 61.1 grams of the subject peracid precursor product again in the form of a white solid.

EXAMPLE 4

2α or β- Decenyl (Mono p-Carboxy Phenol) Succinate

Again, the steps of Example 1 were repeated except that 38.1 grams of decenylsuccinic anhydride were dissolved in THF in place of the octylsuccinic anhydride in Example 1. The decenylsuccinic anhydride was also obtained from Humphrey Chemical Co.

This resulted in formation of 54.2 grams of the subject peracid precursor product in the form of a white solid.

EXAMPLE 5

2α or β- Dodecenyl (Mono p-Carboxy Phenol) Succinate

The steps of Example 1 were again repeated except that 53.2 grams (0.2 moles) of dodecenylsuccinic anhydride were dissolved in the THF. At the same time, the acid was dissolved in 160 milliliters of a 10% solution of sodium hydroxide as also disclosed above in Example 3.

This resulted in formation of 77.8 grams of the subject peracid precursor product again in the form of a white solid.

EXAMPLE 6

2α or β- Tetradecenyl (Mono p-Carboxy Phenol) Succinate

The steps of Example 1 were again repeated with 47 grams (0.16 moles) of tetradecenylsuccinic anhydride, again obtained from Humphrey Chemical Co., being dissolved in the THF. Also as in Examples 3 and 5, the acid was dissolved in 130 milliliters of a 10% solution of sodium hydroxide in water.

This resulted in a the formation of 64 grams of the subject peracid precursor product again in the form of a white solid.

EXAMPLE 7

α and β-Decyl Monophenol Succinate

The steps of Example 1 were again repeated except that 7.2 grams (0.03 moles) of decylsuccinic anhydride were combined with 150 milliliters of diethyl ether. The decylsuccinic anhydride of this example was also obtained from Humphrey Chemical Co. At the same time, 2.3 grams (0.025 moles) of phenol were dissolved in the sodium hydroxide solution. Otherwise, the steps of Example 1 were repeated as noted above, resulting in formation of 9.3 grams of the subject peracid precursor product in the form of a white solid.

EXAMPLE 8

α and β-Dodecyl Monophenol Succinate

The steps of Example 7 were again repeated except that 7.5 grams (0.08 moles) of dodecylsuccinic anhydride were employed in place of decyl succinic anhydride described as above in connection with Example 7. At the same time, the phenol was dissolved in 32 milliliters of a 10% solution of sodium hydroxide in order to provide greater liquid or water volume as was also disclosed above in connection with Examples 3, 5 and 6. Otherwise, the steps of Examples 7 and 1 were again repeated resulting in the formation of 17.2 grams of the subject peracid precursor product in the form of a white solid.

In addition to setting forth specific procedures for forming preferred peracid precursor products according to the present invention, Examples 1 through 8 to further demonstrate the ability to synthesize other peracid precursor products having the general structure set forth above by similar techniques.

The peracid precursor products formed in accordance with Examples 1-8 above were further tested as described below both in terms of perhydrolysis yield and subsequent bleaching characteristics. Those features of the invention for the respective products are set forth immediately below.

Peracid Yield from Perhydrolysis of Different Precursors

The ability of the peracid precursor products of the invention to produce effective peracid yields is demonstrated in Table I below which sets forth yield data for the products described above in Examples 1-8 and also for two peracid precursor products disclosed in the Chung et al reference for purposes of comparison. Accordingly, in Table I, tests carried out with the products of Examples 1-8 are respectively numbered 1-8 with the two Chung et al peracid precursor prodcuts numbered 9 and 10.

Peracid yeilds for these respective products were determined at a number of pH levels to demonstrate the perhydrolysis effectiveness of the peracid precursors at relatively low pH levels in the range of approximately 8 to 10. Accordingly, tests were initially conducted at relatively high pH levels with additional yield tests being conducted at successively lower pH levels until the resulting yield values became unacceptable for one reason or another.

In carrying out the perhydrolysis yield tests, the respective peracid precursors were introduced into an aqueous solution together with a source of hydrogen peroxide. In these tests, for convenience, liquid hydrogen peroxide was employed in a 2:1 molar ratio relative to the precursor. The use of liquid hydrogen peroxide generally simulates wash water conditions where a compound such as sodium perborate is the normal source of hydrogen peroxide.

In actual wash water applications, the peracid precursor would of course be incorporated in a solid composition with or without various surfactants and other detergent adjuncts. However, the test as set forth above provides an effective test indicating perhydrolysis yield for each of the peracid precursors.

In conducting these tests, peracid yields in the soltuions were determined at a number of time intervals by potassium iodide (KI) titration in order to determine active oxygen yields. Such titration tests are well known in the art and are disclosed for example in the publication titled "Peracid and Peroxide Oxidations" by Sheldon N. Lewis (see above). Accordingly, that reference is incorporated herein as though set forth in its entirety.

Peracid yield tests were carried out at three pH levels including pH values of 8.5, 9.5 and 10.5. Tests were first conducted at the highest pH value and then at successively lower pH values. However, if the perhydrolysis yield values fell below an acceptable level, about 40% of theoretical for example, then tests were not carried out at the lower pH levels.

Further in Table I, below, titration to determine active oxygen (A.O.) was carried out for the products of Examples 2-8 and the Chung et al products numbered 9-10. The yields of peracid given in Table I are the maximum amounts formed.

The two precursor products tested from the Chung et al reference included sodium linear octanoyloxybenzene sulfonate (number 9) and sodium linear decanoyloxybenzene sulfonate (number 10).

TABLE I

Comparative Perhydrolysis Yield for Tests Carried Out at 70° F. (or 21° C.) as a Percentage of Theoretical Peracid Active Oxygen

| | % Yield from Titrated A.O. | | |
|---|---|---|---|
| Precursor | pH 8.5 | pH 9.5 | pH 10.5 |
| 2 | 86 | 97 | 100 |
| 3 | — | 37 | 72 |
| 4 | 89 | 87 | 100 |
| 5 | 41 | 70 | 99 |
| 6 | — | — | 30 |
| 7 | — | 82 | 89 |
| 8 | — | — | 31 |
| 9 (Chung et al) | — | 39 | 83 |
| 10 (Chung et al) | — | 26 | 58 |

Table I clearly demonstrates advantages in peracid precursor products of the present invention in producing very high perhydrolysis yields which are generally insensitive to pH.

A comparison of the perhydrolysis yields for peracid precursor products of the present invention considered with respect to yields for products as disclosed by Chung et al further demonstrate the superior characteristics of the precursors of the present invention.

Bleach Performance Tests

Performance tests for the precursors of the present invention were also conducted.

Performance tests summarized in Table II below were carried out as follows: stain removal studies were conducted with a tergotometer (operating at 100 rpm and 100° F. (38° C.).

Wash water containing 1.50 grams per liter (g/L) of Tide ® detergent and 0.02M sodium carbonate was adjusted to the desired pH indicated in Table II by the addition of sulfuric acid or sodium hydroxide. The pH level was maintained throughout a twelve minute wash cycle. A hydrogen peroxide level of 28 parts per million (ppm), measured as active oxygen (A.O.), was developed. A precursor concentration of 14 ppm theoretical A.O. was established by adding either 332/ppm decyl monophenol carboxylate succinic anhydride precursor of 356 ppm dodecyl monophenol carboxylate succinic anhydride precursor, assuming 100% purity.

TABLE II

| | | Percent Stain Removal | |
|---|---|---|---|
| Oxidant | pH | Ink stain | Coffee stain |
| C$_{10}$ MPSAP (Example 2) | 8.5 | 71.4 | 87.6 |
| | 9.9 | 60.5 | 87.0 |
| C$_{12}$ MPSAP (Example 3) | 9.9 | 59.4 | 87.0 |
| Detergent | 9.8 | 55.8 | 83.3 |
| LSD* | | 1.89 | 1.76 |

*Least significant difference at a 95% confidence level.

From these tests, the precursors of the invention were found to exhibit significant improvements in bleaching performance in comparison with detergent alone as demonstrated in Table II.

The foregoing description, embodiments and examples of the invention have been set forth for purposes of illustration and not for the purpose of restricting the scope of the invention. Other non-limiting embodiments of the invention are possible in addition to those set forth above in the description and in the examples. For example as was also noted above, peracid precursor products according to the present invention could be formed by similar synthesis techniques for products having leaving groups Z and R groups as defined above in connection with the general structure of the peracid precursors of the invention. Accordingly, the scope of the present invention is defined only by the following claims which are also further illustrative of the invention.

What is claimed is:

1. A dry bleaching composition comprising a bleach effective amount of a peracid precursor compound of the general structure

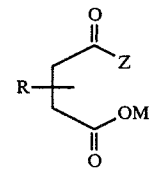

wherein
Z is a leaving group, the conjugate acid of which has a pKa in the range of from about 4 to about 15,
R is a substituted or unsubstituted, alkyl or alkenyl group having from about one to about eighteen carbon atoms, and
M is hydrogen or an alkali or alkaline earth metal; and a source capable of yielding hydrogen peroxide in aqueous solution.

2. The composition of claim 1 wherein the hydrogen peroxide source is selected from the group of alkali metal salts of percarbonate, perborate, persilicate and hydrogen peroxide adjuncts.

3. The composition of claim 2 further comprising a surfactant or polymer.

4. The composition of claim 3 wherein the surfactant is selected from the group consisting of anionic, nonionic, zwitterionic, cationic, amphoteric surfactants and mixtures thereof.

5. The composition of claim 3 wherein the polymer is selected from the group of water soluble polymers consisting of polyvinyl acid, polyacrylic acid and polyvinyl alcohol.

6. The composition of claim 4 wherein Z is selected from the group consisting of:

(1) a compound having the general structure

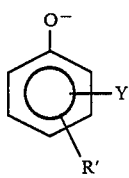

wherein

Y and R' are optionally substituted at any respective locations in the structure, R' is hydrogen or a substituted or unsubstituted alkyl group of about one to ten carbon atoms, with or without an ether linkage, that is, R' or OR' where R' is otherwise defined as above, and Y is hydrogen or a halogen or a solubilizing group;

(2) a compound selected from the group of general structures consisting of:

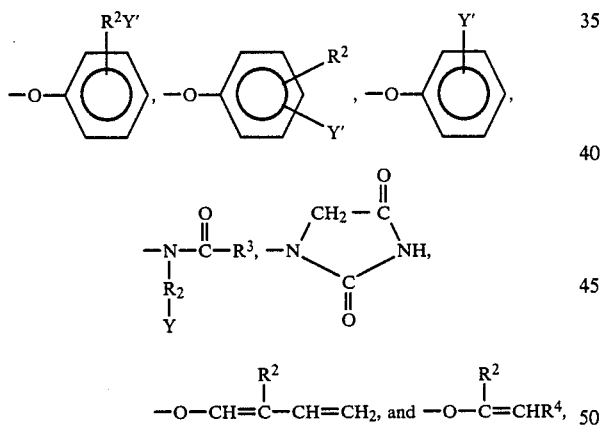

$$-O-CH=\overset{R^2}{\underset{|}{C}}-CH=CH_2, \text{ and } -O-\overset{R^2}{\underset{|}{C}}=CHR^4,$$

wherein $R^2$ is an alkyl chain containing from about one to eight carbon atoms, wherein $R^3$ is an alkyl group containing from about one to eighteen carbon atoms wherein the longest linear alkyl chain extending from and including the carbonyl carbon contains from about six to ten carbon atoms, wherein $R^4$ is H or $R^2$, and wherein Y' is H or a solubilizing group; and (3) the group further consisting of enols, carbon acids and N-alkyl quaternary imidazoles.

7. The composition of calim 6 wherein R is an alkyl group having from about eight to twelve carbon atoms and wherein Z is a compound having the general structure

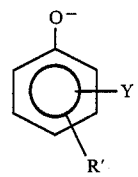

wherein R' and Y are optionally substituted at any available respective locations in the structure.

8. The composition of claim 7 wherein R' is hydrogen and Y is H or $CO_2-M'$, M' being hydrogen or an alkali or alkaline earth metal or mixtures thereof.

9. The composition of claim 6 wherein R is an alkenyl group having from about ten to fourteen carbon atoms and wherein Z is a compound having the general structure

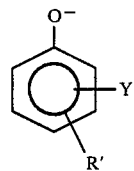

wherein R' and Y are optionally substituted at any available respective locations in the structure.

10. The composition of claim 9 wherein R' is hydrogen and Y is H or $CO_2-M'$, M' being hydrogen or an alkali or alkaline earth metal or mixtures thereof.

11. A method for removing soils from fabrics comprising the step of contacting said fabrics in an aqueous solution with a bleaching composition comprising:

a source capable of yielding hydrogen peroxide in aqueous solution; and a bleach effective amount of a peracid precursor having the general structure

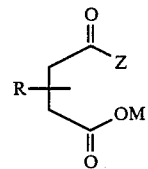

wherein

Z is a leaving group, the conjugate acid of which has a pKa in the range of from about 4 to about 15, R is a substituted or unsubstituted alkyl or alkenyl group having from about one to about eighteen carbon atoms, and M is hydrogen or an alkali or alkaline earth metal.

12. The method of claim 11 wherein the hydrogen peroxide source is selected from the group consisting of alkali metal salts of percarbonate, perborate, persilicate and hydrogen peroxide adjuncts.

13. The method of claim 11 further comprising a surfactant or polymer selected for stability of the precursor and surfactant.

14. The method of claim 13 wherein the surfactant is selected from the group consisting of anionic, nonionic, zwitterionic, cationic, amphoteric surfactants and mixtures thereof.

15. The method of claim 13 wherein the polymer is selected from the group of water soluble polymers consisting of polyvinyl acid, polyacrylic acid and polyvinyl alcohol.

16. The method of claim 11 where Z is selected from the group consisting of:

(1) a compound having the general structure

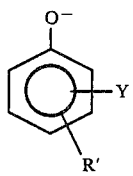

wherein

Y and R' are optionally substituted at any respective locations in the structure, R' is hydrogen or a substituted or unsubstituted alkyl group of about one to about ten carbon atoms, with or without an ether linkage, that is, R' or OR' where R' is otherwise defined as above, and Y is hydrogen or a halogen or a solubilizing group; and (2) a compound selected from the group consisting of:

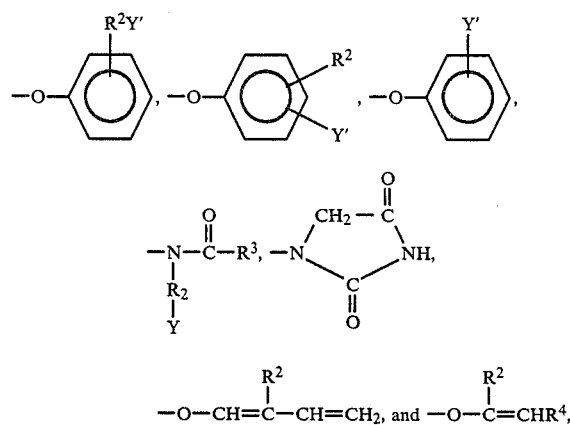

wherein $R^2$ is an alkyl chain containing from about one to about eight carbon atoms, $R^3$ is an alkyl group containing from about one to about eighteen carbon atoms wherein the longest linear alkyl chain extending from and including the carbonyl carbon contains from about six to ten carbon atoms, $R^4$ is H or $R^2$, and Y is H or a solubilizing group; and (3) the group further consisting of enols, carbon acids and N-alkyl quaternary imidazoles.

17. The method of claim 16 wherein R is an alkyl group having from about eight to twelve carbon atoms and wherein Z is a compound having the general structure

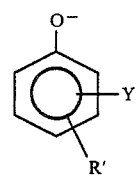

wherein R' and Y are optionally substituted at any available respective locations in the structure.

18. The method of claim 17 wherein R' is hydrogen and Y is H or $CO_2-M'$, M' being hydrogen or an alkali or alkaline earth metal or mixtures thereof.

19. The method of claim 16 wherein R is an alkenyl group having from about ten to fourteen carbon atoms and wherein Z is a compound having the general structure:

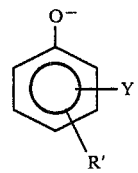

wherein R' and Y are optionally substituted at any available respective locations in the structure.

20. The method of claim 19 wherein R' is hydrogen and Y is H or $CO_2-M'$, M' being hydrogen or an alkali or alkaline earth metal or mixtures thereof.

* * * * *